United States Patent [19]

Loncrini et al.

[11] 4,309,564

[45] Jan. 5, 1982

[54] METHODS FOR PREPARING EUTECTIC MIXTURES OF P-HYDROXYBENZOIC ACID ESTERS

[75] Inventors: Donald F. Loncrini, Ellisville; John J. Taylor, St. Peters, both of Mo.

[73] Assignee: Mallinckrodt, Inc., St. Louis, Mo.

[21] Appl. No.: 199,719

[22] Filed: Oct. 23, 1980

[51] Int. Cl.$^3$ ............................................. C07C 69/88
[52] U.S. Cl. ..................................................... 560/67
[58] Field of Search ........................................ 560/67

[56] References Cited

U.S. PATENT DOCUMENTS 2,350,326 6/1944 Du Vall et al. ...................... 560/67
3,097,131 7/1963 Ueno et al. ........................... 562/601
3,321,509 5/1967 Burris et al. ........................... 560/67

*Primary Examiner*—Paul J. Killos

*Attorney, Agent, or Firm*—Senniger, Powers, Leavitt and Roedel

[57] ABSTRACT

Novel methods of forming in situ eutectic mixtures of three or more lower alkyl esters of p-hydroxybenzoic acid are disclosed which avoid the prior art methods of forming the respective esters independently and blending them, for example, by melting. Such eutectic mixtures may be formed in situ by first reacting a p-hydroxybenzoic acid and a lower alkanol in the presence of an esterification catalyst to form a first lower alkyl ester of p-hydroxybenzoic acid, reacting the resulting mixture with two or more lower alkanols under heat to form a mixture of three or more lower alkyl esters of p-hydroxybenzoic acid, quenching the reaction when the ratio of the respective lower alkyl esters of p-hydroxybenzoic acid to each other is such that the mixture thereof is liquid at room temperature and isolating the resulting eutectic mixture. Other methods of preparing such eutectic mixtures in situ are also disclosed.

28 Claims, No Drawings

METHODS FOR PREPARING EUTECTIC MIXTURES OF P-HYDROXYBENZOIC ACID ESTERS

BACKGROUND OF THE INVENTION

This invention relates to liquid eutectic mixtures and more particularly, to liquid eutectic mixtures of lower alkyl esters of p-hydroxybenzoic acid such as isopropyl p-hydroxybenzoate, isobutyl p-hydroxybenzoate, n-butyl p-hydroxybenzoate, sec-butyl p-hydroxybenzoate and amyl p-hydroxybenzoate, and to methods of preparing such mixtures in situ with the components in the desired ratio to render the mixture liquid at room temperature.

As is known, p-hydroxybenzoic acid alkyl esters, such as isopropyl p-hydroxybenzoate, isobutyl p-hydroxybenzoate and n-butyl p-hydroxybenzoate, are useful as antimicrobial agents, for example, in the form of emulsions. Such esters have generally been used individually, are sparsely soluble in water and are usually solid at room temperature.

In U.S. Pat. No. 3,097,131, there are disclosed eutectic mixtures of esters of p-hydroxybenzoic acid which are liquid at room temperature and which are stated to overcome the drawbacks and inconveniences inherent in the conventional independent use of such esters. These mixtures are formed by mixing two or more independently prepared esters of p-hydroxybenzoic acid (e.g., n-butyl p-hydroxybenzoate, sec-butyl p-hydroxybenzoate and isobutyl p-hydroxybenzoate) and heating the mixture to melt and allowing the melt to cool to room temperature or by tritulating a mixture of such esters in a mortar at room temperature until the mixture melts.

However, heretofore, there has not been available practical means for forming room-temperature liquid eutectic mixtures of p-hydroxybenzoic acid alkyl esters in situ starting with p-hydroxybenzoic acid and the respective alcohols such as isopropyl, isobutyl and n-butyl, sec-butyl and amyl alcohols.

SUMMARY OF THE INVENTION

Among the several objects of the invention may be noted the provision of methods for forming in situ eutectic mixtures of lower alkyl esters of p-hydroxybenzoic acid; the provision of such methods for forming eutectic mixtures having the desired ratios of the respective lower alkyl esters of the mixture; and the provision of such methods which permit the ready recovery of unreacted p-hydroxybenzoic acid. Other objects and features will be in part apparent and in part pointed out hereinafter.

Briefly, the present invention is directed to the method of forming in situ eutectic mixtures of three or more lower alkyl esters of p-hydroxybenzoic acid, such as for example mixtures of isopropyl p-hydroxybenzoate, isobutyl p-hydroxybenzoate and n-butyl p-hydroxybenzoate, which comprises reacting p-hydroxybenzoic acid and a lower alkanol in the presence of an esterification catalyst to form a first lower alkyl ester of p-hydroxybenzoic acid, reacting the resulting mixture with two or more lower alkanols under heat to form a mixture of three or more lower alkyl esters of p-hydroxybenzoic acid, quenching the reaction when the ratio of the respective lower alkyl esters of p-hydroxybenzoic acid to each other is such that the mixture thereof is liquid at room temperature and isolating the resulting eutectic mixture.

The invention is also directed to forming in situ eutectic mixtures of three or more lower alkyl esters of p-hydroxybenzoic acid by reacting p-hydroxybenzoic acid and three or more lower alkanols in the presence of an esterification catalyst to form a mixture of three or more lower alkyl esters of p-hydroxybenzoic acid, quenching the reaction when the ratio of the respective lower alkyl esters of p-hydroxybenzoic acid to each other is such that the mixture thereof is liquid at room temperature and isolating the resulting eutectic mixture.

The invention is further directed to forming in situ eutectic mixtures of three or more lower alkyl esters of p-hydroxybenzoic acid by reacting a lower alkyl ester of p-hydroxybenzoic acid with three or more lower alkanols in the presence of an esterification catalyst to form a mixture of three or more lower alkyl esters of p-hydroxybenzoic acid derived from said lower alkanols, quenching the reaction when the ratio of the respective lower alkyl esters to each other is such that the mixture thereof is liquid at room temperature and isolating the resulting eutectic mixture.

DESCRIPTION OF THE PREFERRED EMBODIMENTS

In accordance with the present invention, it has now been found that eutectic mixtures of three or more lower alkyl esters of p-hydroxybenzoic acid which are liquid at room temperature may be conveniently and economically formed in situ by several methods which avoid the separate and independent preparation and isolation of each ester and subsequent blending thereof by melting the individual esters as described in the prior art. As used herein, the term "eutectic mixture" means that the mixture is liquid at room temperature which renders the formulation of such a mixture into antimicrobial compositions convenient and simple.

In a first and preferred aspect of the invention, the eutectic mixtures of three or more lower alkyl esters of p-hydroxybenzoic acid are formed by reacting p-hydroxybenzoic acid and a lower alkanol, such as isopropyl alcohol, in the presence of an esterification catalyst to form a first lower alkyl ester of p-hydroxybenzoic acid, such as isopropyl p-hydroxybenzoate, reacting the resulting mixture with two or more lower alkanols (e.g., isobutyl alcohol, n-butyl alcohol, sec-butyl alcohol, amyl alcohol, hexyl alcohol (hexanol), etc.) under heat to form a mixture of three or more lower alkyl esters of p-hydroxybenzoic acid. As used herein, the term "lower alkyl" means alkyl groups containing 1 to 6 carbon atoms and, similarly, the term "lower alkanol" means alcohols or alkanols containing 1 to 6 carbon atoms. Thus, the invention is generally applicable to the formation in situ of eutectic mixtures of three or more lower alkyl esters of p-hydroxybenzoic acid, such esters including, for example, isopropyl p-hydroxybenzoate, isobutyl p-hydroxybenzoate, n-butyl p-hydroxybenzoate, amyl p-hydroxybenzoate, and so forth. As indicated, the lower alkanol reacted with p-hydroxybenzoic acid in the first aspect of the invention can be any one of the various lower alkanols containing 1 to 6 carbon atoms including, without limitation, methyl alcohol, ethyl alcohol, propyl alcohol, isopropyl alcohol, n-butyl alcohol, isobutyl alcohol, sec-butyl alcohol, amyl alcohol, hexyl alcohol and their respective isomers.

After the p-hydroxybenzoic acid and a lower alkanol have been reacted, as described, to form a first lower alkyl ester of p-hydroxybenzoic acid, the resulting mixture is reacted with two or more lower alkanols under heat to form a mixture of three or more lower alkyl esters of p-hydroxybenzoic acid. Alternatively, and within the scope of the invention, the first lower alkyl ester of p-hydroxybenzoic acid may be independently prepared and then reacted with two or more lower alkanols. This reaction involves both esterification of the lower alkanols and transesterification of the lower alkyl ester (e.g., isopropyl p-hydroxybenzoate) of p-hydroxybenzoic acid.

Then, the reaction is quenched when the ratio of the respective lower alkyl esters of p-hydroxybenzoic acid to each other is such that the mixture is liquid at room temperature. This ratio can be readily determined by experimentation for each mixture of three or more lower alkyl esters of p-hydroxybenzoic acid within the purview of the invention. Once the desired ratio has been achieved, the eutectic mixture can then be isolated.

Thus, through the present invention, such eutectic mixtures useful as antimicrobial compositions for food, pharmaceutical and cosmetic applications may be formed directly without the necessity of forming and isolating the individual esters separately and then melting or otherwise blending them together to form liquid eutectic mixtures.

As a specific example of the first aspect of the invention, it has now been found that eutectic mixtures of isopropyl p-hydroxybenzoate, isobutyl p-hydroxybenzoate and n-butyl p-hydroxybenzoate in a ratio between approximately 1:1:1 and 4:2:2, respectively, which are liquid at room temperature, may be conveniently and economically formed in situ by reacting p-hydroxybenzoic acid and isopropyl alcohol in the presence of an esterification catalyst to form isopropyl p-hydroxybenzoate, reacting the resulting mixture with isobutyl alcohol and n-butyl alcohol under heat, quenching the reaction when the ratio of isopropyl p-hydroxybenzoate to isobutyl p-hydroxybenzoate to n-butyl p-hydroxybenzoate is within the desired range between approximately 1:1:1 and 4:2:2 and thereafter isolating the resulting eutectic mixture.

As stated, in this example of the preferred embodiment of the invention, p-hydroxybenzoic acid and isopropyl alcohol are first reacted in the presence of an esterification catalyst to form isopropyl p-hydroxybenzoate. In this step, the mixture of p-hydroxybenzoic acid, isopropyl alcohol and the catalyst is charged to a flask, stirred, heated to reflux and then held at reflux for a sufficient period, generally 8 hours, to obtain maximum esterification of the p-hydroxybenzoic acid to the desired isopropyl p-hydroxybenzoate. Any esterification catalyst known to those skilled in the art may be generally used in practicing the invention, including sulfuric acid, sulfonic acids, sulfonic acid resins and p-toluene sulfonic acid. Sulfuric acid is preferred because of its ready availability.

After the desired isopropyl p-hydroxybenzoate has been formed as described, isobutyl alcohol and n-butyl alcohol are added and the resulting mixture is stirred, heated and distilled to a pot temperature of approximately 118° C. In this step, transesterification of isopropyl p-hydroxybenzoate and esterification of p-hydroxybenzoic acid by isobutyl alcohol and n-butyl alcohol occur at the same time. Depending upon the ratio of isopropyl p-hydroxybenzoate to isobutyl p-hydroxybenzoate to n-butyl p-hydroxybenzoate desired, the reaction is either quenched at this point or refluxed for an additional period of time. As shown by working examples 1–4, 6 and 7 hereinafter, the ratio of the above esters in the eutectic mixture formed will vary according to the time of reflux as follows:

| Example | Reflux | Ratio of isopropyl p-hydroxybenzoate: isobutyl p-hydroxybenzoate:n-butyl p-hydroxybenzoate |
| --- | --- | --- |
| 1 | 2½ hrs. | 4:3.54:3.99 |
| 2 | ½ hr. | 4:3.3:3.47 |
| 3 | 0 | 4:1.81:1.92 |
| 4 | 1 hr. | 4:3.88:3.85 |
| 6 | 0 | 4:1.83:1.91 |
| 7 | ½ hr. | 4:2.82:2.88 |

As can be seen, the longer the reaction is allowed to proceed by refluxing, the closer the ratio of the respective esters will approach the ratio 4:4:4 (or 1:1:1). Conversely, when the reaction is quenched without refluxing or further heating, the closer the ratio of the respective esters will approach 4:2:2.

During the distillation step, the temperature of the flask or pot may vary from a low of approximately 95° C. up to 118° C. and the distillate may contain, for example, a mixture of isopropyl alcohol, water and other components such as isopropyl ether.

At the desired time for quenching the reaction as indicated, the contents of the flask, principally the eutectic mixture of the three noted p-hydroxybenzoates considered in this example of the invention, unreacted p-hydroxybenzoic acid and unreacted isopropyl alcohol, isobutyl alcohol and n-butyl alcohol are added to distilled water (e.g., 2 liters) containing citric acid (e.g., 50 g). This stops or quenches the reaction 5 and forms a two-phase system, the upper phase being an oil phase containing the eutectic mixture and some unreacted alcohol and the lower phase being an aqueous phase containing water, unreacted alcohol, sulfuric acid and citric acid. The citric acid functions as a chelating agent for any impurities such as iron.

At this point, an alkali metal hydroxide, such as sodium hydroxide, is added to the system to bring the pH to 7.5–8.0 and neutralize sulfuric acid, citric acid and any unreacted p-hydroxybenzoic acid. After this step, the aqueous phase is still the lower phase and the eutectic oil phase is still the upper phase.

These phases are then separated and the aqueous phase is acidified, as by adding sulfuric acid, to produce free p-hydroxybenzoic acid. The aqueous phase is then cooled, the solids filtered off, washed, dried and weighed as recovered unreacted p-hydroxybenzoic acid which can then be reused.

The oil or organic phase containing the eutectic mixture is washed with water to remove any salts such as sodium sulfate and sodium p-hydroxybenzoate. This produces a two-layer system in which the organic phase is the lower phase and the aqueous phase is the upper phase. These layers are then separated and the aqueous layer discarded. The oil layer is then transferred to a flask, water is added and the mixture distilled at atmospheric pressure to remove any unreacted alcohols. The resulting eutectic mixture of isopropyl p-hydroxybenzoate, isobutyl p-hydroxybenzoate and n-butyl p-hydroxybenzoate in the form of an oil is then dried.

The illustrative eutectic mixtures resulting from the methods of the invention containing isopropyl p-hydroxybenzoate, isobutyl p-hydroxybenzoate and n-butyl p-hydroxybenzoate in a ratio between approximately 1:1:1 and 4:2:2 are liquid at room temperature and may withstand temperatures down to at least 0° C. without freezing. Mixtures below a ratio of 4:2:2 are generally not stable liquids since they tend to crystallize after prolonged standing at room temperature. Mixtures above a ratio of 1:1:1, while remaining liquids, are generally not desirable due to the decrease in water solubility. Eutectic mixtures formed in situ by the methods of the invention may be used to formulate emulsions utilized as antimicrobial compositions in various food, pharmaceutical and cosmetic applications.

From the standpoint of water solubility referring to this illustrative embodiment of the invention, it is preferred that the invention be practiced to form eutectic mixtures having a ratio of 4:2.5:2.5 isopropyl p-hydroxybenzoate:isobutyl p-hydroxybenzoate:n-butyl p-hydroxybenzoate. A eutectic mixture with this ratio has a water solubility on the order of 0.06% to 0.07% while mixtures having ratios above the stated range of 4:2.5:2.5 are generally less soluble. Likewise, mixtures having ratios below the range of 4:2.5:2.5 are generally more soluble.

It will be understood that similar considerations apply to the formation of other eutectic mixtures of three or more lower alkyl esters of p-hydroxybenzoic acid in accordance with the invention.

In a second but less preferred aspect of the invention, the eutectic mixtures are formed in situ by reacting p-hydroxybenzoic acid and three or more lower alkanols in the presence of an esterification catalyst to form a mixture of three or more lower alkyl esters of p-hydroxybenzoic acid. The reaction basically involves esterification of the three or more lower alkanols. In this aspect of the invention, the reaction is again quenched when the ratio of the respective lower alkyl esters of p-hydroxybenzoic acid to each other is such that the mixture thereof is liquid at room temperature.

As a specific example of this aspect of the invention, p-hydroxybenzoic acid is reacted with all three or more alcohols (e.g., isopropyl alcohol, isobutyl alcohol and n-butyl alcohol) in the presence of an esterification catalyst in a single step. The resulting reaction mixture is then treated as before to obtain eutectic mixtures having a ratio of the three esters within the range previously stated and which are liquid at room temperature. Eutectic mixtures formed in this manner tend to have a ratio on the order of 1:1:1 isopropyl p-hydroxybenzoate:isobutyl p-hydroxybenzoate:n-butyl p-hydroxybenzoate and are less water soluble than those having a ratio on the order of 4:2.5:2.5.

In still another but less preferred aspect of the invention, eutectic mixtures of three or more lower alkyl esters of p-hydroxybenzoic acid are formed in situ by reacting a lower alkyl ester of p-hydroxybenzoic acid such as methyl p-hydroxybenzoate with three or more lower alkanols, such as isopropyl alcohol, isobutyl alcohol and n-butyl alcohol, in the presence of an esterification catalyst. In this aspect of the invention, it will be appreciated that the reaction is basically a transesterification reaction with no p-hydroxybenzoic acid per se being present.

For example, methyl p-hydroxybenzoate may be reacted with isopropyl alcohol, isobutyl alcohol and n-butyl alcohol in the presence of an esterification catalyst. The desired eutectic mixture of isopropyl p-hydroxybenzoate, isobutyl p-hydroxybenzoate and n-butyl p-hydroxybenzoate is then formed by transesterification of the methyl p-hydroxybenzoate and is isolated as previously described. This method is less preferred for forming eutectic mixtures having ratios of the respective esters within the aforementioned range.

Another useful feature of the invention is that eutectic mixtures having different ratios of the respective esters within the aforementioned range may be readily blended to provide eutectic mixtures having more desirable solubility properties. Thus, for example, appropriate amounts of a eutectic mixture having a ratio of 4:4:4 (1:1:1) and one having a ratio of 4:2:2 may be blended to produce a eutectic mixture having a ratio on the order of 4:2.5:2.5. Since these respective eutectic mixtures are liquid at room temperature, they may be readily blended to produce a eutectic mixture with the desired ratio of the respective esters. Further, a eutectic mixture having a ratio outside the range of approximately 1:1:1 to 4:2:2 may be blended with additional amounts of isopropyl p-hydroxybenzoate, isobutyl p-hydroxybenzoate or n-butyl p-hydroxybenzoate to form a eutectic mixture having a ratio of the respective esters within the stated range.

The following examples further illustrate the practice of the invention.

EXAMPLE 1

A 5-liter flask was set up in a heating mantle equipped with mechanical stirring, a thermometer and a condenser. Into the flask was charged p-hydroxybenzoic acid (1200 g) isopropyl alcohol (1600 g) and concentrated sulfuric acid (200 g). The mixture was stirred, heated to reflux and held at reflux for 8 hours.

To the resulting mixture was added isobutyl alcohol (576 g) and n-butyl alcohol (512 g). The mixture was stirred, heated to boiling and distilled to a pot temperature of 118° C. After 1940 ml had been distilled at vapor temperatures from 98.5° to 108.2° C., the mixture was switched to reflux and held at reflux for 2½ hours. The pot temperature fell to 110° C.

The reaction mixture was then poured equally into two 4-liter beakers, each containing 1 liter of distilled water and 25 g of citric acid. 50% Sodium hydroxide (410 g) was added to bring the pH to 7.5 to 8.0.

The contents of both beakers were transferred to a 6-liter separatory funnel and the bottom aqueous layer separated from the top organic layer. The aqueous layer was transferred to a 4-liter beaker, stirred and sulfuric acid added until the pH was approximately 1. The layer was then cooled, the solids filtered off, washed, dried and weighed as recovered p-hydroxybenzoic acid (152 g, 12.67%).

The organic layer was washed twice with 1 liter of water containing sodium chloride. The aqueous layer as then separated and discarded. The organic layer was then transferred to a 5-liter flask set up in a heating mantle. The layer was stirred and heated to distill water and the isobutyl and n-butyl alcohols and azeotroped with 300–500 ml of distilled water twice at a maximum pot temperature of 104° C.

The remaining product was filtered hot and weighed. The product weighed 1427 g for a yield of 87.1%. Liquid chromatography showed that the resulting eutectic mixture had a ratio of 4:3.54:3.99 isopropyl p-hydroxybenzoate:isobutyl p-hydroxybenzoate:n-butyl p-hydroxybenzoate.

EXAMPLE 2

Example 1 was repeated except as follows.

The same amounts of p-hydroxybenzoic acid, isopropyl alcohol and sulfuric acid were charged and the mixture was stirred, heated to reflux and held at reflux for 8 hours. To the resulting mixture was added isobutyl alcohol (576 g) and n-butyl alcohol (496 g.). The resulting mixture was heated to boiling and distilled to a pot temperature of 118° C. After 1925 ml had been distilled at temperatures from 97° C. to 118° C., the mixture was switched to reflux for one-half hour. The reaction mixture was then quenched and 50% sodium hydroxide (380 g.) added to bring the pH to 7.5–8.0. The layers were separated and the aqueous layer acidified to recover the unreacted p-hydroxybenzoic acid (121 g, 10.08%).

The eutectic oil layer was washed with 1 liter of water containing sodium chloride. The resulting layers were separated and the aqueous layer discarded. The oil layer containing the esters of p-hydroxybenzoic acid was then transferred to a 3-liter round-bottom 3-neck flask using 300 ml of water. The mixture was stirred and heated under vacuum and distilled to remove any remaining butyl alcohols as an azeotrope with water. The distillation was repeated with a second 300 ml of water. The product was filtered and weighed 1477 g. Liquid chromatography showed that the resulting eutectic mixture had a ratio of 4:3.3:3.47 isopropyl p-hydroxybenzoate:isobutyl p-hydroxybenzoate:n-butyl p-hydroxybenzoate.

EXAMPLE 3

Example 1 was repeated except as follows.

The same amounts of p-hydroxybenzoic acid, isopropyl alcohol and sulfuric acid were charged and the mixture was stirred, heated to reflux and held at reflux for 8 hours. To the resulting mixture was added isobutyl alcohol (576 g) and n-butyl alcohol (488 g), the mixture was heated to boiling and distilled to a pot temperature of 118° C. After 1800 ml had been distilled at temperatures from 95° C. to 118.5° C., the reaction mixture was quenched and 50% sodium hydroxide (300 g) added to bring the pH to 7.5–8.0. The layers were then separated. The eutectic oil layer was washed with 400 ml of distilled water and heated under vacuum to remove the butyl alcohols as an azeotrope. The aqueous layer was acidified to recover the unreacted p-hydroxybenzoic acid (46 g, 3.83%). The oil layer was filtered and weighed. Liquid chromatography showed the eutectic mixture had a ratio of 4:1.8:1.9 isopropyl p-hydroxybenzoate:isobutyl p-hydroxybenzoate:n-butyl p-hydroxybenzoate.

EXAMPLE 4

Example 1 was repeated except as follows:

The same amounts of p-hydroxybenzoic acid, isopropyl alcohol and sulfuric acid were charged and the mixture was stirred, heated to reflux and held at reflux for 8 hours. To the resulting mixture was added isobutyl alcohol (576 g) nd n-butyl alcohol (484 g). The mixture was stirred, heated to boiling and distilled to a pot temperature of 118° C. After 1870 ml had been distilled at temperatures from 96° C. to 118° C., the mixture was switched to reflux and held at reflux for 1 hour at a pot temperature of 115° C. The reaction was quenched and 50% sodium hydroxide (370 g) added to bring the pH to 7.5–8.0. The layers were worked up as before and the unreacted p-hydroxybenzoic acid (118 g, 9.8%) was recovered.

The oil layer was transferred to a 3-liter flask, distilled water (400 ml) was added and the mixture was stripped under vacuum to a pot temperature of 120° C. The oil layer was cooled, filtered and weighed (1431 g). Liquid chromatography showed the eutectic mixture had a ratio of 4:3.88:3.85 isopropyl p-hydroxybenzoate:isobutyl p-hydroxybenzoate:n-butyl p-hydroxybenzoate.

EXAMPLE 5

The eutectic mixture of Example 2 (10 g) was mixed with the eutectic mixture of Example 3 (10 g) and liquid chromatography showed that the resulting mixture had a ratio of 4:2.41:2.56 isopropyl p-hydroxybenzoat:isobutyl p-hydroxybenzoate:n-butyl p-hydroxybenzoate versus a calculated ratio of 4:2.56:2.70. The eutectic mixture (19 g) formed in the above step was then mixed with the eutectic mixture of Example 2 (19 g) and liquid chromatography showed that the resulting mixture had a ratio of 4:2.83:3.00 isopropyl p-hydroxybenzoate:isobutyl p-hydroxybenzoate:n-butyl p-hydroxybenzoate versus a calculated ratio of 4:2.93:3.08.

EXAMPLE 6

Example 1 was repeated except as follows:

The same amounts of p-hydroxybenzoic acid, isopropyl alcohol and sulfuric acid were charged and the mixture was stirred, heated to reflux and held at reflux for 8 hours. To the resulting mixture was added isobutyl alcohol (576 g) and n-butyl alcohol (484 g) after which the mixture was stirred, heated to boiling and distilled to a pot temperature of 118° C. After 1925 ml had been distilled at temperatures from 94° C. to 118° C., the reaction was quenched and worked up as before. Unreacted p-hydroxybenzoic acid (58 g, 4.83%) was recovered.

The oil layer was transferred to a 3-liter flask, distilled water (400 ml) was added and the mixture stripped under vacuum to a pot temperature of approximately 120° C. This step was repeated after which ethyl alcohol (200 ml) was added and the resulting mixture again stripped under vacuum to a pot temperature of approximately 120° C. The oil layer was filtered and weighed (1524 g). Liquid chromatography showed the eutectic mixture had a ratio of 4:1.83:1.91 isopropyl p-hydroxybenzoate:isobutyl p-hydroxybenzoate:n-butyl p-hydroxybenzoate which corresponds very closely to the ratio for the eutectic mixture of Example 3.

EXAMPLE 7

Example 6 was repeated except as follows:

The same amounts of p-hydroxybenzoic acid, isopropyl alcohol, sulfuric acid, isobutyl alcohol and n-butyl alcohol were used. After 1860 ml had been distilled at temperature from 96° C. to 118° C., the reaction was switched to reflux and held at reflux for 30 minutes. The reaction mixture was then quenched and worked up as before. Unreacted p-hydroxybenzoic acid (100 g, 8.33%) was recovered.

Distilled water (400 ml) was added to the oil layer and the mixture distilled under atmospheric pressure at a pot temperature of 103° C. (vapor temperature 97° C.) until a vapor temperature of 100° C. was obtained. A full vacuum was then applied and the mixture distilled to a pot temperature of approximately 120° C. The product was filtered and weighed (1463 g). Liquid chromatography showed the eutectic mixture had a ratio of 4:2.82:2.88 isopropyl p-hydroxybenzoate:isobutyl p-hydroxybenzoate:n-butyl p-hydroxybenzoate.

EXAMPLE 8

Example 6 was again repeated except as follows.

The same amounts of p-hydroxybenzoic acid, isopropyl alcohol, sulfuric acid, isobutyl alcohol and n-butyl alcohol were used. After 1750 ml had been distilled at temperatures from 96° C. to 118° C., the reaction was switched to reflux and held at reflux for 15 minutes at a pot temperature of 116° C. The reaction was then quenched in distilled water (2 liters) containing citric acid (50 g). The mixture was stirred and 50% sodium hydroxide (318 g) was added to bring the pH to 7.0–7.5.

The bottom aqueous layer was separated from the upper oil layer. The aqueous layer was transferred to a 4-liter beaker, stirred, sulfuric acid added to bring the pH to 1.0, cooled to approximately 20° C., stirred for one-half to one hour, filtered, washed, dried and weighed to recover unreacted p-hydroxybenzoic acid (72 g, 6.0%).

The oil layer was washed once with 50°–60° C. distilled water (2 liters) to produce a mixture in which the upper layer was aqueous and the bottom layer was the oil layer. The bottom layer was separated and transferred to a 3-liter, 3-neck round-bottom flask using distilled water (400 ml). The mixture was stirred, heated to boiling and distilled at atmospheric pressure to a pot temperature of 120° C. to remove excess butyl alcohols (300 ml alcohol, 475 ml water). This step was repeated with additional distilled water (400 ml). A full vacuum was applied to dry the oil at a final pot temperature of approximately 125° C. The oil was filtered and weighed (1508 g). Liquid chromatography showed the eutectic mixture had a ratio of 4:2.2:2.3 isopropyl p-hydroxybenzoate:isobutyl p-hydroxybenzoate:n-butyl p-hydroxybenzoate.

EXAMPLE 9

Example 8 was repeated using the same amounts of p-hydroxybenzoic acid, isopropyl alcohol, sulfuric acid, isobutyl alcohol and n-butyl alcohol and the same general reaction and separation procedures.

Unreacted p-hydroxybenzoic acid (76.2 g, 6.4%) was recovered as before.

Liquid chromatography showed the eutectic mixture obtained had a ratio of 4:2.3:2.4 isopropyl p-hydroxybenzoate:isobutyl p-hydroxybenzoate:n-butyl p-hydroxybenzoate.

EXAMPLE 10

Example 8 was repeated using the same amounts of p-hydroxybenzoic acid, isopropyl alcohol, sulfuric acid, isobutyl alcohol and n-butyl alcohol and the same general reaction and separation procedures, except that after 1900 ml had been distilled at pot temperatures from 92° C. to 118° C., the reaction was not switched to reflux but quenched.

Unreacted p-hydroxybenzoic acid (62 g, 5.2%) was recovered as before.

Liquid chromatography showed the eutectic mixture obtained had a ratio of 4:2.1:2.2 isopropyl p-hydroxybenzoate:isobutyl p-hydroxybenzoate:n-butyl p-hydroxybenzoate.

EXAMPLE 11

Example 8 was repeated using the same amounts of p-hydroxybenzoic acid, isopropyl alcohol, sulfuric acid, isobutyl alcohol and n-butyl alcohol and the same general reaction and separation procedures, except that after 1650 ml had been distilled at pot temperatures from 94° C. to 118° C., the reaction was held at reflux for 20 minutes before being quenched.

Unreacted p-hydroxybenzoic acid (60 g, 5.0%) was recovered as before.

Liquid chromatography showed the eutectic mixture obtained had a ratio of 4:2.0:2.1 isopropyl p-hydroxybenzoate:isobutyl p-hydroxybenzoate:n-butyl p-hydroxybenzoate.

EXAMPLE 12

Example 8 was repeated using the same amounts of p-hydroxybenzoic acid, isopropyl alcohol, sulfuric acid isobutyl alcohol and n-butyl alcohol and the same general reaction and separation procedures, except that after 1800 ml had been distilled at pot temperatures from 94° C. to 118° C., the reaction was held at reflux for 30 minutes before being quenched.

Unreacted p-hydroxybenzoic acid (86 g, 7.17%) was recovered as before.

Liquid chromatography showed the eutectic mixture obtained had a ratio of 4:2.9:2.9 isopropyl p-hydroxybenzoate:isobutyl p-hydroxybenzoate:n-butyl p-hydroxybenzoate.

EXAMPLE 13

A 1-liter, 3-neck round bottom flask was set up in a heating mantle and equipped with mechanical stirring, a thermometer, a Dean & Stark tube and a condenser. To the flask was charged p-hydroxybenzoic acid (150 g), isopropyl alcohol (220 g), isobutyl alcohol (36 g), n-butyl alcohol (36 g), sulfuric acid (25 g) and toluene (50 ml). The mixture was stirred, heated to reflux, set for distillation and distilled to a pot temperature of 119° C. After distillation for approximately 1 hour and 38 minutes at temperatures from 95° C. to 127.5° C., the reaction was poured into approximately 200 ml of water, stirred and 50% sodium hydroxide added to bring the pH to 7.5–8.0. The oil layer was separated, washed with hot water and the eutectic oil collected and dried. Before and after drying, the ratio of isopropyl p-hydroxybenzoate to isobutyl p-hydroxybenzoate to n-butyl p-hydroxybenzoate was found to be 3.1:3.2:3.7.

107 g of the oil was transferred to a beaker and 5.35 g of isobutyl p-hydroxybenzoate and 19.6 g of isopropyl p-hydroxybenzoate were added. The resulting mixture was stirred and heated to obtain a solution. Liquid chromatography showed that the resulting eutectic mixture had an isopropyl p-hydroxybenzoate:isobutyl p-hydroxybenzoate:n-butyl p-hydroxybenzoate ratio of 4:2.4:2.3.

EXAMPLE 14

Methyl p-hydroxybenzoate (100 g) was charged to a 500-ml 3-neck flask equipped with mechanical stirring, a thermometer and a condenser which could be set for reflux or distillation. To the flask was charged isopropyl alcohol (25.95 g), n-butyl alcohol (21.35 g) and isobutyl alcohol (21.35 g). The mixture was stirred and concentrated sulfuric acid (15 g) was added. Stirring was continued and the mixture heated to reflux and held at reflux for 8 hours at pot temperatures of 106° C. to 125° C. with two intermittent distillations of 2 g and 5 g, respectively. The heating was stopped and the reaction mixture allowed to cool. The reaction mixture was poured into distilled water (150 ml), the resulting mixture stirred and citric acid (2-3 g) added. Stirring was continued and 50% sodium hydroxide added to bring the pH to 7.5-8.0. The eutectic oil layer was separated and washed with hot distilled water. The oil was separated and dried overnight at approximately 80° C. in a tared dish to yield 88 g of the eutectic oil.

EXAMPLE 15

A 500-ml, 3-neck round bottom flask was set up in a heating mantle and equipped with a thermometer, mechanical stirring and a condenser. To the flask was charged p-hydroxybenzoic acid (120 g), isobutyl alcohol (60 g), n-butyl alcohol (45 g), sec-butyl alcohol (55 g) and concentrated sulfuric acid (20 g). The mixture was stirred and heated to reflux at 115° C. After two hours and fifteen minutes, an additional 25 g of sec-butyl-alcohol was added and the mixture heated to reflux at 180° C. After an additional 2 hours and 15 minutes, 40 g of sec-butyl alcohol was added and the mixture heated to reflux at 105° C. After an additional 3 hours, heating was stopped and the mixture allowed to stand overnight. The reaction mixture was then poured into 400 ml of distilled water containing citric acid (10 g). The resulting mixture was stirred, heated to 60°-70° C. and 50% sodium hydroxide added to bring the pH to 7.5-8.0. The mixture was transferred to a separatory funnel and the bottom aqueous layer was separated from the upper organic layer. The organic layer was washed with 400 ml of distilled water and the aqueous layer separated. The organic or oil phase was then transferred to a 3-neck flask, 100 ml of water was added and the mixture distilled to a pot temperature of approximately 120° C. Another 100 ml of water was added and the mixture again distilled to a pot temperature of approximately 120° C. A vacuum was applied and the product heated to approximately 150° C. The product was cooled to approximately 90° C. and filtered. 117 g of the eutectic oil was obtained. Liquid chromatography showed that the resulting eutectic mixture had a sec-butyl p-hydroxybenzoate:isobutyl p-hydroxybenzoate:n-butyl p-hydroxybenzoate ratio of 2.3:4:2.83.

EXAMPLE 16

A 500 ml, 3-neck round bottom flask was set up in a heating mantle and equipped with a thermometer, mechanical stirring and a condenser. To the flask was charged p-hydroxybenzoic acid (120 g), isopropyl alcohol (160 g) and concentrated sulfuric acid (20 g). The mixture was stirred, heated to reflux and held at reflux for 8 hours. To the resulting mixture was added sec-butyl alcohol (60 g) and amyl alcohol (60 g). The mixture was stirred and heated to reflux at 115° C. After 2 hours and 10 minutes, additional sec-butyl alcohol (30 g) was added and the mixture heated to reflux at 110° C. After an additional 2 hours and 50 minutes, heating was discontinued and the mixture allowed to stand overnight. The mixture was then stirred and heated to reflux at 110° C. for 1 hour, sec-butyl alcohol (30 g) was added and the mixture refluxed for another hour at 107° C. The reaction mixture was poured into water containing citric acid, and neutralized to a pH of 7.5-8.0 with 50% sodium hydroxide. The aqueous layer was separated and the organic or oil layer was distilled with additional water. After two distillations to a pot temperature of approximately 120° C., a vacuum was applied to dry the oil. Liquid chromatography showed that the resulting eutectic mixture had an isopropyl p-hydroxybenzoate:sec-butyl p-hydroxybenzoate:amyl p-hydroxybenzoate ratio of 4:1.8:4.8.

EXAMPLE 17

A 500 ml, 3-neck round bottom flask was set up in a heating mantle and equipped with a thermometer, mechanical stirring and a condenser. To the flask was charged isopropyl p-hydroxybenzoate (90.1 g), isobutyl alcohol (22 g), n-butyl alcohol (22 g) and concentrated sulfuric acid (15 g). The mixture was stirred and heated to reflux for 4 hours at vapor temperatures of 81°-86° C. The heating was discontinued and the reaction mixture allowed to cool below 80° C. The reaction mixture was poured into approximately 150 ml of distilled water, stirred and 50% sodium hydroxide was added to bring the pH to 7.5-8.0. The layers were separated and the oil layer washed once with hot (80° C.) distilled water. The layers were again separated and the oil dried at 60°-70° C. in a tared dish. Liquid chromatography showed that the resulting eutectic mixture had an isopropyl p-hydroxybenzoate-isobutyl p-hydroxybenzoate:n-butyl p-hydroxybenzoate ratio of 6.14:41.23:52.63.

In view of the above it will be seen that the several objects of the invention are achieved and other advantageous results attained.

As various changes could be made in the above methods without departing from the scope of the invention, it is intended that all matter contained in the above description shall be interpreted as illustrative and not in a limiting sense.

What is claimed is:

1. The method of forming in situ eutectic mixtures of three or more lower alkyl esters of p-hydroxybenzoic acid which comprises reacting p-hydroxybenzoic acid and a lower alkanol in the presence of an esterification catalyst to form a first lower alkyl ester of p-hydroxybenzoic acid, reacting the resulting mixture with two or more lower alkanols under heat to form a mixture of three or more lower alkyl esters of p-hydroxybenzoic acid, quenching the reaction when the ratio of the respective lower alkyl esters of p-hydroxybenzoic acid to each other is such that the mixture thereof is liquid at room temperature and isolating the resulting eutectic mixture.

2. The method as set forth in claim 1 wherein the esterification catalyst is concentrated sulfuric acid.

3. The method as set forth in claim 1 wherein the pH of the reaction mixture is adjusted to approximately 7.5-8.0 after quenching.

4. The method as set forth in claim 3 wherein quenching of the reaction produces an aqueous layer and an organic eutectic oil layer, the layers are separated and the aqueous layer is acidified to recover unreacted p-hydroxybenzoic acid.

5. The method as set forth in claim 4 wherein the aqueous layer is acidified with sulfuric acid.

6. The method as set forth in claim 1 wherein the lower alkanols reacted with said resulting mixture are selected from the group consisting of propyl alcohol, isopropyl alcohol, n-butyl alcohol, sec-butyl alcohol, amyl alcohol and hexyl alcohol.

7. The method of forming in situ eutectic mixtures of isopropyl p-hydroxybenzoate, isobutyl p-hydroxybenzoate and n-butyl p-hydroxybenzoate in a ratio between approximately 1:1:1 and 4:2:2, respectively, which comprises reacting p-hydroxybenzoic acid and isopropyl alcohol in the presence of an esterification catalyst to form isopropyl p-hydroxybenzoate, reacting the resulting mixture with isobutyl alcohol and n-butyl alcohol under heat, quenching the reaction when the ratio of isopropyl p-hydroxybenzoate to isobutyl p-hydroxybenzoate to n-butyl p-hydroxybenzoate is within the range between approximately 1:1:1 and 4:2:2 and isolating the resulting eutectic mixture.

8. The method as set forth in claim 7 wherein the esterification catalyst is concentrated sulfuric acid.

9. The method as set forth in claim 7 wherein the reaction between p-hydroxybenzoic acid and isopropyl alcohol is held at reflux for approximately 8 hours.

10. The method as set forth in claim 7 wherein the eutectic mixture formed contains isopropyl p-hydroxybenzoate, isobutyl p-hydroxybenzoate and n-butyl p-hydroxybenzoate in a ratio of approximately 4:2.5:2.5.

11. The method as set forth in claim 7 wherein the pH of the reaction mixture is adjusted to approximately 7.5–8.0 after quenching.

12. The method as set forth in claim 11 wherein quenching of the reaction produces an aqueous layer and an organic eutectic oil layer, the layers are separated and the aqueous layer is acidified to recover unreacted p-hydroxybenzoic acid.

13. The method as set forth in claim 12 wherein the aqueous layer is acidified with sulfuric acid.

14. The method as set forth in claim 7 wherein the eutectic mixture as initially formed has a ratio of isopropyl p-hydroxybenzoate to isobutyl p-hydroxybenzoate to n-butyl p-hydroxybenzoate outside the range of approximately 1:1:1 to 4:2:2 and is blended with additional amounts of isopropyl p-hydroxybenzoate, isobutyl p-hydroxybenzoate or n-butyl p-hydroxybenzoate to form a eutectic mixture having a ratio of said respective components within said range.

15. The method of forming in situ eutectic mixtures of three or more lower alkyl esters of p-hydroxybenzoic acid which comprises reacting p-hydroxybenzoic acid and three or more lower alkanols in the presence of an esterification catalyst to form a mixture of three or more lower alkyl esters of p-hydroxybenzoic acid, quenching the reaction when the ratio of the respective lower alkyl esters of p-hydroxybenzoic acid to each other is such that the mixture thereof is liquid at room temperature and isolating the resulting eutectic mixture.

16. The method as set forth in claim 15 wherein the esterification catalyst is concentrated sulfuric acid.

17. The method as set forth in claim 15 wherein the lower alkanols are selected from the group consisting of propyl alcohol, isopropyl alcohol, n-butyl alcohol, sec-butyl alcohol, amyl alcohol and hexyl alcohol.

18. The method of forming in situ eutectic mixtures of isopropyl p-hydroxybenzoate, isobutyl p-hydroxybenzoate and n-butyl p-hydroxybenzoate in a ratio between approximately 1:1:1 and 4:2:2, respectively, which comprises reacting p-hydroxybenzoic acid, isopropyl alcohol, isobutyl alcohol and n-butyl alcohol in the presence of an esterification catalyst, quenching the reaction when the ratio of isopropyl p-hydroxybenzoate to isobutyl p-hydroxybenzoate to n-butyl p-hydroxybenzoate is within the range between approximately 1:1:1 and 4:2:2 and isolating the resulting eutectic mixture.

19. The method as set forth in claim 18 wherein the esterification catalyst is concentrated sulfuric acid.

20. The method as set forth in claim 18 wherein the eutectic mixture formed contains isopropyl p-hydroxybenzoate, isobutyl p-hydroxybenzoate and n-butyl p-hydroxybenzoate in a ratio of approximately 4:2.5:2.5.

21. The method as set forth in claim 18 wherein the eutectic mixture as initially formed has a ratio of isopropyl p-hydroxybenzoate to isobutyl p-hydroxybenzoate to n-butyl p-hydroxybenzoate outside the range of approximately 1:1:1 to 4:2:2 and is blended with additional amounts of isopropyl p-hydroxybenzoate, isobutyl p-hydroxybenzoate or n-butyl p-hydroxybenzoate to form a eutectic mixture having a ratio of said respective components within said range.

22. The method of forming in situ eutectic mixtures of three or more lower alkyl esters of p-hydroxybenzoic acid which comprises reacting a lower alkyl ester of p-hydroxybenzoic acid with three or more lower alkanols in the presence of an esterification catalyst to form a mixture of three or more lower alkyl esters of p-hydroxybenzoic acid derived from said lower alkanols, quenching the reaction when the ratio of the respective lower alkyl esters of p-hydroxybenzoic acid to each other is such that the mixture thereof is liquid at room temperature and isolating the resulting eutectic mixture.

23. The method as set forth in claim 22 wherein the esterification catalyst is concentrated sulfuric acid.

24. The method as set forth in claim 22 wherein the lower alkanols are selected from the group consisting of propyl alkcohol, isopropyl alcohol, n-butyl alcohol, sec-butyl alcohol, amyl alcohol and hexyl alcohol.

25. The method of forming in situ eutectic mixtures of isopropyl p-hydroxybenzoate, isobutyl p-hydroxybenzoate and n-butyl p-hydroxybenzoate in a ratio between approximately 1:1:1 and 4:2:2, respectively, which comprises reacting methyl p-hydroxybenzoate with isopropyl alcohol, isobutyl alcohol and n-butyl alcohol in the presence of an esterification catalyst, quenching the reaction when the ratio of isopropyl p-hydroxybenzoate to isobutyl p-hydroxybenzoate to n-butyl p-hydroxybenzoate is within the range between approximately 1:1:1 and 4:2:2 and isolating the resulting eutectic mixture.

26. The method as set forth in claim 25 wherein the esterification catalyst is concentrated sulfuric acid.

27. The method as set forth in claim 25 wherein the eutectic mixture formed contains isopropyl p-hydroxybenzoate, isobutyl p-hydroxybenzoate and n-butyl p-hydroxy benzoate in a ratio of approximately 4:2.5:2.5.

28. The method as set forth in claim 25 wherein the eutectic mixture as initially formed has a ratio of isopropyl p-hydroxybenzoate to isobutyl p-hydroxybenzoate to n-butyl p-hydroxybenzoate outside the range of approximately 1:1:1 to 4:2:2 and is blended with additional amounts of isopropyl p-hydroxybenzoate, isobutyl p-hydroxybenzoate or n-butyl p-hydroxybenzoate to form a eutectic mixture having a ratio of said respective components within said range.

* * * * *